(12) United States Patent
Suzuki et al.

(10) Patent No.: US 10,977,806 B2
(45) Date of Patent: Apr. 13, 2021

(54) EYE MOVEMENT FEATURE AMOUNT CALCULATING SYSTEM, EYE MOVEMENT FEATURE AMOUNT CALCULATING METHOD, AND NON-TRANSITORY COMPUTER-READABLE STORAGE MEDIUM

(71) Applicant: HAMAMATSU PHOTONICS K.K., Hamamatsu (JP)

(72) Inventors: Kazutaka Suzuki, Hamamatsu (JP); Haruyoshi Toyoda, Hamamatsu (JP); Hiroyuki Okada, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 49 days.

(21) Appl. No.: 16/367,586

(22) Filed: Mar. 28, 2019

(65) Prior Publication Data

US 2019/0311484 A1 Oct. 10, 2019

(30) Foreign Application Priority Data

Apr. 10, 2018 (JP) .............................. JP2018-075388

(51) Int. Cl.
*G06T 7/00* (2017.01)
*G06T 7/246* (2017.01)
*A61B 5/16* (2006.01)

(52) U.S. Cl.
CPC .............. *G06T 7/246* (2017.01); *A61B 5/163* (2017.08); *G06T 7/0016* (2013.01); *G06T 2207/30041* (2013.01)

(58) Field of Classification Search
CPC ................... G06T 7/246; G06T 7/0016; G06T 2207/30041; A61B 5/163
See application file for complete search history.

(56) References Cited

U.S. PATENT DOCUMENTS

| 10,117,577 | B2 * | 11/2018 | Mochizuki | ......... | G02B 27/0101 |
| 2015/0073575 | A1 * | 3/2015 | Sarkis | .................... | G11B 27/02 |
| | | | | | 700/94 |

(Continued)

FOREIGN PATENT DOCUMENTS

JP WO2020188629 A1 * 9/2020 ............... A61B 5/16

OTHER PUBLICATIONS

Suzuki, Kazutaka et al., "Development of Binocular Microsaccade Measurement System Using Intelligent Vision Sensor and Evaluation of Synchronization between Left and Right Microsaccades," Transactions of Japanese Society for Medical and Biological Engineering, 53, 5, 2015, pp. 247-254.

*Primary Examiner* — Khai M Nguyen
(74) *Attorney, Agent, or Firm* — Faegre Drinker Biddle & Reath LLP

(57) ABSTRACT

An eye movement feature amount calculating system includes: a moving state input unit that inputs moving state values in a time series indicating a moving state of an eye of an examinee; a saccade period extracting unit that extracts a saccade period in which the eye performs saccadic movement based on time-series variation of the moving state values; and a feature amount calculating unit that divides a period including at least a part of the extracted saccade period into a plurality of periods and calculates a feature amount of eye movement of the subject based on the separate periods.

9 Claims, 7 Drawing Sheets

(56) References Cited

U.S. PATENT DOCUMENTS

2018/0125357 A1* 5/2018 Suzuki .................. A61B 3/113
2020/0139112 A1* 5/2020 Aharonovitch .... A61N 1/36031
2020/0192478 A1* 6/2020 Alcaide ................. A61B 3/113
2020/0305708 A1* 10/2020 Krueger ................ G06F 3/012

* cited by examiner

EYE MOVEMENT FEATURE AMOUNT CALCULATING SYSTEM, EYE MOVEMENT FEATURE AMOUNT CALCULATING METHOD, AND NON-TRANSITORY COMPUTER-READABLE STORAGE MEDIUM

TECHNICAL FIELD

The present invention relates to an eye movement feature amount calculating system, an eye movement feature amount calculating method, and a non-transitory computer-readable storage medium that calculate a feature amount of the eye movement of a subject.

BACKGROUND

In the related art, technology of detecting a micro-saccade which is one type of involuntary eye movement has been proposed. For example, Kazutaka SUZUKI, Haruyoshi TOYODA, Ryohei HANAYAMA, and Katsuhiro ISHII, "Development of Binocular Microsaccade Measurement System Using Intelligent Vision Sensor and Evaluation of Synchronization between Left and Right Microsaccades," Transactions of Japanese Society for Medical and Biological Engineering, 53, 5, pp. 247-254, 2015, which is Non-patent Document 1, discloses that binocular micro-saccades of an examinee are detected and differences therebetween are analyzed.

SUMMARY

A decrease in the quality of life of patients and families thereof due to contracting dementia can be avoided by early detection and proper treatment. Positron emission tomography (PET) examination is effective for early detection of dementia. However, the number of facilities that can carry out PET examination is limited and all persons requiring examination may not be able to be examined due to inspection costs, required times, or the like. Prescreening technology for allowing efficient usage of examination facilities and objectively presenting the necessity for examination and priorities can improve such circumstances.

An eye is an organ which is directly coupled to the brain and which is differentiated from the brain in the course of growing of an embryo. There are many related art examples suggesting a relationship between abnormality of the brain and eye movement. Therefore, it is conceivable that brain disorders such as dementia may be prescreened based on a micro-saccade which is described in Non-patent Document 1. In the related research other than that described in Non-patent Document 1, a maximum speed, a period, a moving distance, and a saccade direction are used for evaluation of a micro-saccade. However, satisfactory prescreening cannot be performed by only detecting micro-saccades and utilizing feature amounts thereof.

The invention is made in consideration of the above-mentioned circumstances and an objective thereof is to provide an eye movement feature amount calculating system, an eye movement feature amount calculating method, and a non-transitory computer-readable storage medium that can calculate a feature amount of eye movement which can be appropriately used to determine a brain state or the like.

In order to achieve the above-mentioned objective, an eye movement feature amount calculating system according to an embodiment of the invention includes circuitry configured to: input moving state values in a time series indicating a moving state of an eye of a subject; extract a saccade period in which the eye performs saccadic movement based on time-series variation of the moving state values; and divide a period including at least a part of the saccade period into a plurality of periods and calculates a feature amount of eye movement of the subject based on the separate periods.

In the eye movement feature amount calculating system according to the embodiment of the invention, a feature amount of eye movement of a subject is calculated based on periods into which a period including at least a part of a saccade period is divided. The inventor of the present invention found that it is possible to more appropriately perform determination of a brain state or the like by using the feature amount based on the separate periods than, for example, by using a feature amount based on the entire saccade period. Accordingly, with the eye movement feature amount calculating system according to the embodiment of the invention, it is possible to more appropriately calculate a feature amount of eye movement which can be used for determination of a brain state or the like.

The circuitry may be further configured to divide the period including at least a part of the saccade period into a plurality of periods based on the time-series variation of the moving state values in the saccade period. Specifically, the circuitry may be further configured to divide the period into a first half period and a second half period at a time at which the moving state value in the saccade period is a maximum. According to this configuration, it is possible to appropriately and certainly divide the period and thus to more appropriately calculate a feature amount of eye movement which can be used for determination of a brain state or the like.

The circuitry may be further configured to calculate a value based on the moving state values for each of the separate periods and calculate the feature amount of the eye movement of the subject by comparing the calculated values for the separate periods. According to this configuration, it is possible to more appropriately calculate a feature amount of eye movement which can be used for determination of a brain state or the like.

The circuitry may be further configured to input a value indicating a speed of the eye as the moving state value. According to this configuration, it is possible to appropriately and certainly calculate a feature amount of eye movement.

The circuitry may be further configured to determine a brain state of the subject based on the feature amount. According to this configuration, it is possible to appropriately determine a brain state of a subject using the calculated feature amount.

The circuitry may be further configured to measure the moving state of the eye of the subject and generate the moving state value. According to this configuration, it is possible to certainly input moving state values and to carry out the embodiment of the invention.

On the other hand, the invention can be described as an invention of an eye movement feature amount calculating system as described above and can also be described as inventions of an eye movement feature amount calculating method and a non-transitory computer-readable storage medium as will be described below. These inventions are different in only category and are the same invention and can achieve the same operations and advantages.

That is, an eye movement feature amount calculating method according to an embodiment of the invention includes: inputting moving state values in a time series indicating a moving state of an eye of a subject; extracting a saccade period in which the eye performs saccadic movement based on time-series variation of the moving state values; and dividing a period including at least a part of the saccade period into a plurality of periods and calculating a feature amount of eye movement of the subject based on the separate periods.

That is, a non-transitory computer-readable storage medium storing an eye movement feature amount calculating program according to an embodiment of the invention causes a computer to execute: moving state input function of inputting moving state values in a time series indicating a moving state of an eye of a subject; saccade period extracting function of extracting a saccade period in which the eye performs saccadic movement based on time-series variation of the moving state values; and feature amount calculating function of dividing a period including at least a part of the saccade period into a plurality of periods and calculates a feature amount of eye movement of the subject based on the separate periods.

According to the embodiment of the invention, it is possible to calculate a feature amount of eye movement which can be appropriately used to determine a brain state or the like.

DETAILED DESCRIPTION

Hereinafter, an eye movement feature amount calculating system, an eye movement feature amount calculating method, and a non-transitory computer-readable storage medium according to an embodiment of the present invention will be described in detail with reference to the accompanying drawings. In description with reference to the drawings, the same elements will be referred to by the same reference signs and description thereof will not be repeated.

Figure 1:
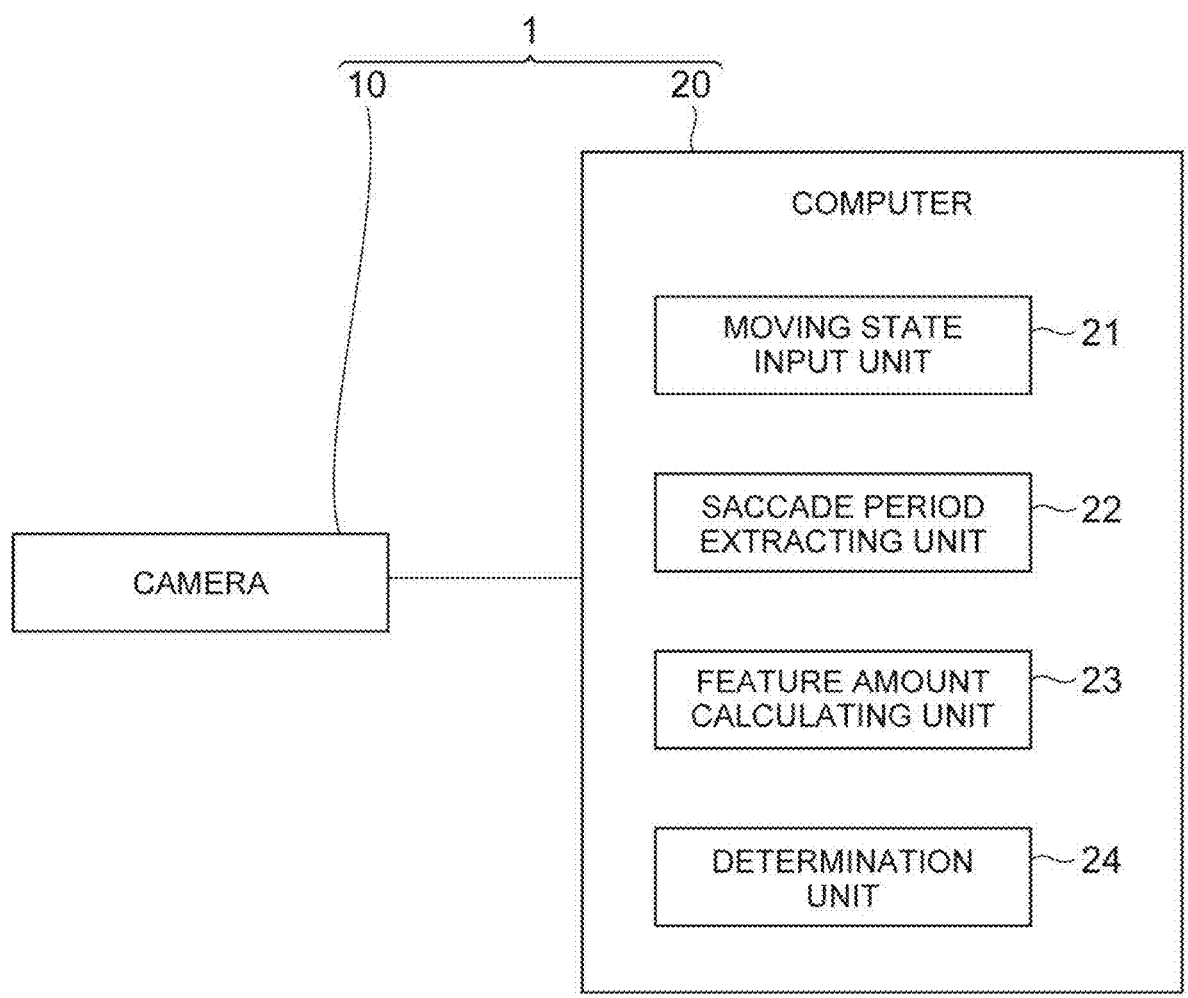
FIG. 1 is a diagram illustrating a configuration of an eye movement feature amount calculating system according to an embodiment of the present invention.

An eye movement feature amount calculating system 1 according to an embodiment is illustrated in FIG. 1. The eye movement feature amount calculating system 1 includes a camera 10 and a computer 20. The eye movement feature amount calculating system 1 according to this embodiment is a system (a device) that measures eye movement of an examinee (a subject) and calculates feature amounts of the eye movement. The eye movement feature amount calculating system 1 determines a brain state of the examinee based on the calculated feature amounts.

This determination is determination of whether some disorder has occurred in the brain function. Specifically, this determination is determination of whether an examinee has a disease associated with the brain function such as dementia, depression, higher brain dysfunction, or Alzheimer's disease. In order to accurately determine the disease, it is normally necessary to perform examination such as PET examination. Determination by the eye movement feature amount calculating system 1 according to this embodiment is performed, for example, as prescreening for determining whether such examination is necessary.

Eye movement which is measured by the eye movement feature amount calculating system 1 according to this embodiment is small saccadic movement (micro-saccadic movement) which is saccadic eye movement and is, for example, a micro-saccade (flick) which is one type of involuntary eye movement which is involuntarily performed during fixation.

The camera 10 is an imaging device that images an eye of an examinee. The camera 10 is moving state measuring means that measures moving states of an eye of an examinee and generates moving state values in a time series indicating each the moving state of the eye of the examinee. The camera 10 continuously performs capturing an image to detect eye movement of an examinee. Cameras in the related art can be used as the camera 10 and, for example, cameras that can capture an image at a high frame rate at which a micro-saccade can be detected can be used. Since a micro-saccade is often performed in about 20 msec, for example, a camera 10 that can capture an image at several hundreds of Hz to about 1000 Hz can be used as the camera 10. Cameras that can capture an image at a frame rate other than described above may be used as the camera 10.

Capturing an image by the camera 10 may be performed on only one eye (only one eye may be measured) or may be simultaneously performed on both eyes (both eyes may be simultaneously measured). When both eyes are simultaneously imaged, right and left eyes may be independently imaged using two or more cameras 10 which are synchronized to simultaneously image movement of both eyes or which have been ascertained to be able to measure both eyes in synchronization with each other or both eyes may be simultaneously imaged using one camera 10.

For example, by using a multi-eye IVS camera system of an intelligent vision sensor (IVS) made by Hamamatsu Photonics K.K., eye movement of both eyes of an examinee can be simultaneously measured in a state in which imaging times of two cameras have been synchronized with each other. When two cameras of a high resolution type are independently used, the variation between clocks of the IVS cameras is equal to or less than 10 ppm. This value corresponds to 0.03 msec or less in three-second measurement in which a margin of one second is added to two seconds generally called an occurrence frequency of a micro-saccade. Accordingly, it is possible to simultaneously perform measurement with satisfactorily time accuracy. There is a likelihood that moving image data output from the IVS cameras will vary by a maximum of 0.5 frames from each other, which is less than one frame and which does not cause a problem.

When it is intended to measure both eyes using one camera, this measurement can be realized, for example, using a CMOS area image sensor S13101 made by Hamamatsu Photonics K.K. An S13101 has a pixel resolution which is four times that of the above-mentioned IVS camera and can read only an image of a required position at a high speed. By imaging an area, which has been imaged using two IVS cameras, using one camera and outputting only an eye image, it is possible to realize fast measurement over a long time.

For example, a position of corneal reflected light which is reflected by a cornea is detected as an eye position from an image captured by the camera 10. Therefore, when capturing an image is performed by the camera 10, an illumination for generating corneal reflected light may be provided. The light intensity and the emission wavelength of the illumination and the like may be adjusted such that a luminance distribution of the reflected light image becomes a Gaussian distribution in detecting the position of a cornea. An illumination for imaging an eye and enabling adjustment of a relative position between the eye and the camera 10 may be provided. The reason for preparing a plurality of illuminations is that a light intensity with which the whole eye can be recognized may not be obtained with only an illumination for generating corneal reflected light. Adjustment of the relative position between an examinee and the camera 10 may be performed in a state that the whole eye can be recognized. This is because a light intensity becomes insufficient with only one illumination for generating corneal reflected light when a high-speed camera is used. However, when the camera 10 has sufficient light sensitivity, a plurality of illuminations are not necessary. By decreasing the frame rate of the camera 10 when the relative position between an examinee and the camera 10 is adjusted and increasing the frame rate of the camera 10 at the time of measurement, it is not necessary to prepare a plurality of illuminations.

As an examinee gazes at a visual target installed in front of the examinee during measurement, it is possible to realize stable measurement without causing a sight to lurch. For example, a chip light emitting diode (chip LED) may be used for the visual target. By disposing a lens between the LED and an examinee's eye and providing a mechanism that adjusts a distance between the lens and the LED, a visual target, in which the LED can be recognized at infinity without affecting the examinee's visual power, can be realized. A coefficient for calculating a change of an eye position which is not affected by the curvature of a cornea can be calculated from a change in position of corneal reflected light when target LEDs are disposed at four corners in the front of an examinee and at the center thereof and the LEDs are turned on.

When an image of an examinee's eye is captured by the camera 10, a motion of a face may be simultaneously measured. A camera for measuring a motion of a face may be additionally provided or an eye measuring camera which has already been provided may be used. When a motion of a face is measured, a wrinkle on the skin, an eyebrow, an eyelash, an injury, a mole, a freckle, or the like may be tracked, or a lens close to the radius of curvature of a cornea may be attached between the eyebrows and a position change of reflected light thereof may be calculated as a motion of a face. The measured motion of a face is used, for example, for correcting an eye position due to a motion of a face.

The camera 10 detects a moving state of an examinee's eye from each captured image and generates moving state values in a time series indicating each the moving state of the examinee's eye. A moving state value is a physical quantity indicating a moving state, and is a speed of an eye (an eye movement speed) in this embodiment. The camera 10 includes a processor that performs image processing or the like (for example, an IVS) and calculates a speed of an eye as follows.

The camera 10 detects (measures) an eye position (a coordinate position in an image) from each captured image (each frame). As described above, the position of corneal reflected light is detected as an eye position. Detection of an eye position can be performed using an arbitrary method in the related art. At this time, correction of the eye position based on a motion of a face may be performed. Correction of an eye position can be performed using an arbitrary method in the related art. The camera 10 calculates an eye movement speed from a change of the eye positions over time. For example, the camera 10 calculates an eye movement speed by calculating a distance between an eye position calculated from each image and an eye position calculated from an immediately previous image (an immediately previous frame) and dividing the distance by the time between frames. By calculating the eye movement speed for each image, eye movement speeds in a time series is obtained. An example of the calculated eye movement speeds is shown in the graph illustrated in FIG. 2. In the graph, the horizontal axis represents time (msec) (for example, an elapsed time from the imaging start) and the vertical axis represents the eye movement speed (degree/second). Each of points in the graph illustrated in FIG. 2 correspond to each of images.

Capturing an image using the camera 10 may be performed, for example, over a preset time (for example, several tens of seconds). Alternatively, the capturing of an image may be performed until a micro-saccade is extracted a predetermined number of times (for example, five times) using the function of the computer 20 which will be described later.

The camera 10 and the computer 20 are connected to each other via a cable or the like and can mutually transmit and receive information. The camera 10 transmits information indicating the calculated eye movement speeds in a time series to the computer 20. Calculation of an eye movement speed need not necessarily be performed by the camera 10 and may be performed by the computer 20. In this case, a captured image is output from the camera 10 to the computer 20.

Detection of an eye position and calculation of an eye movement speed are not necessarily performed with the above-mentioned configuration, and may be performed with an arbitrary method in the related art. For example, an object to be measured may not be the above-mentioned corneal reflected light and may be the center of an area which is obtain by ellipse approximation of an pupillary area or may be a midpoint of a pupil diameter or the center or the gravitational center of a pupil.

The computer 20 is a device that calculates feature amounts of eye movement based on an input from the camera 10 and determines a brain state of an examinee. The computer 20 includes hardware such as a central processing unit (CPU), a memory, and a communication module. The functions of the computer 20 which will be described later are exhibited by causing such elements to operate in accordance with a program or the like. Examples of the computer 20 include a server device and a personal computer (PC). The computer 20 may be constituted by a field programmable gate array (FPGA), a microcomputer, or the like. The computer 20 may be a portable terminal such as a smartphone or a tablet terminal. When a portable terminal has the above-mentioned function of the camera, the portable terminal may be used as the eye movement feature amount calculating system 1.

As illustrated in FIG. 1, the computer 20 functionally includes a moving state input unit 21, a saccade period extracting unit 22, a feature amount calculating unit 23, and a determination unit 24.

The moving state input unit 21 is moving state input means that inputs information indicating eye movement speeds in a time series of an examinee. The moving state input unit 21 receives and inputs information indicating eye movement speeds in a time series which is transmitted from the camera 10. The moving state input unit 21 outputs the input information indicating the eye movement speeds to the saccade period extracting unit 22.

The saccade period extracting unit 22 is saccade period extracting means that extracts a saccade period in which an eye performs a micro-saccade based on timer-series variation of the eye movement speeds indicated by the information input from the moving state input unit 21. The saccade period extracting unit 22 extracts the saccade period, for example, as follows.

The saccade period extracting unit 22 receives an input of information indicating eye movement speeds in a time series from the moving state input unit 21. The saccade period extracting unit 22 compares the eye movement speed at each time with a threshold value. The saccade period extracting unit 22 extracts a period in which the eye movement speed is continuously greater than the threshold value as a saccade period associated with one micro-saccade. The threshold value may be set to a predetermined value and stored in the saccade period extracting unit 22 in advance. Alternatively, the saccade period extracting unit 22 may perform measurement for setting a threshold value before main measurement and calculate the threshold value based on eye movement speeds in a time series. For example, as described in Non-patent Document 1, five times the standard deviation of the eye movement speeds in a time series may be set as the threshold value. This is for stably detecting a micro-saccade without being affected by a change in an eye position due to a drift of involuntary eye movement which differs depending on measurement and variation due to a motion of a head.

Since a micro-saccade is generally maintained for a predetermined time or more, the saccade period extracting unit 22 may not determine a period which is extracted using the threshold value and which is not equal to or greater than a predetermined length, which is noise, as a saccade period. A period which is extracted using the threshold value may include a period of eye movement other than eye movement of which feature amounts will be calculated (which will be measured). Therefore, the saccade period extracting unit 22 may extract a period in which eye movement of which feature amounts will be calculated is performed from the period based on eye movement speeds or the like in the extracted period (that is, a period of eye movement other than eye movement of which feature amounts will be calculated may be excluded). As described above, in this embodiment, a micro-saccade which is involuntary eye movement is set as an object of which feature amounts will be calculated. However, the period extracted using the threshold value may include a period of voluntary eye movement (for example, a voluntary saccade). In general, a voluntary saccade has a higher maximum saccadic speed than an involuntary micro-saccade. Accordingly, both saccades can be separated depending on the maximum speed. For example, the saccade period extracting unit 22 may exclude a period in which a maximum speed of eye movement speeds in the extracted period is greater than a predetermined threshold value as a period of eye movement other than eye movement of which feature amounts will be calculated and may extract a saccade period associated with a micro-saccade.

The saccade period extracting unit 22 outputs information indicating the eye movement speeds in a time series input from the moving state input unit 21 and the extracted saccade period to the feature amount calculating unit 23. When a plurality of saccade periods can be extracted from a series of eye movement speeds in a time series, the saccade period extracting unit 22 outputs information indicating the extracted saccade period to the feature amount calculating unit 23 for each of the plurality of saccade periods.

The feature amount calculating unit 23 is feature amount calculating means that divides a period including at least a part of the saccade period extracted by the saccade period extracting unit 22 into a plurality of periods and calculates feature amounts of eye movement of an examinee based on the separate periods. That is, the feature amount calculating unit 23 quantizes transitional information in saccadic movement. The feature amount calculating unit 23 may divide a period including at least a part of the saccade period into a plurality of periods based on time-series variation of the eye movement speeds in the saccade period extracted by the saccade period extracting unit 22. The feature amount calculating unit 23 may divide the period into a first half period and a second half period at a time at which the eye movement speed has a maximum value (a maximum speed) in the saccade period. The feature amount calculating unit 23 may calculate feature amounts based on the eye movement speeds in the separate periods. The feature amount calculating unit 23 may calculate a value based on the eye movement speeds for each of the separate periods and calculate feature amounts through comparison of the calculated values in the separate periods. The feature amount calculating unit 23 calculates feature amounts, for example, as follows.

Figure 2:
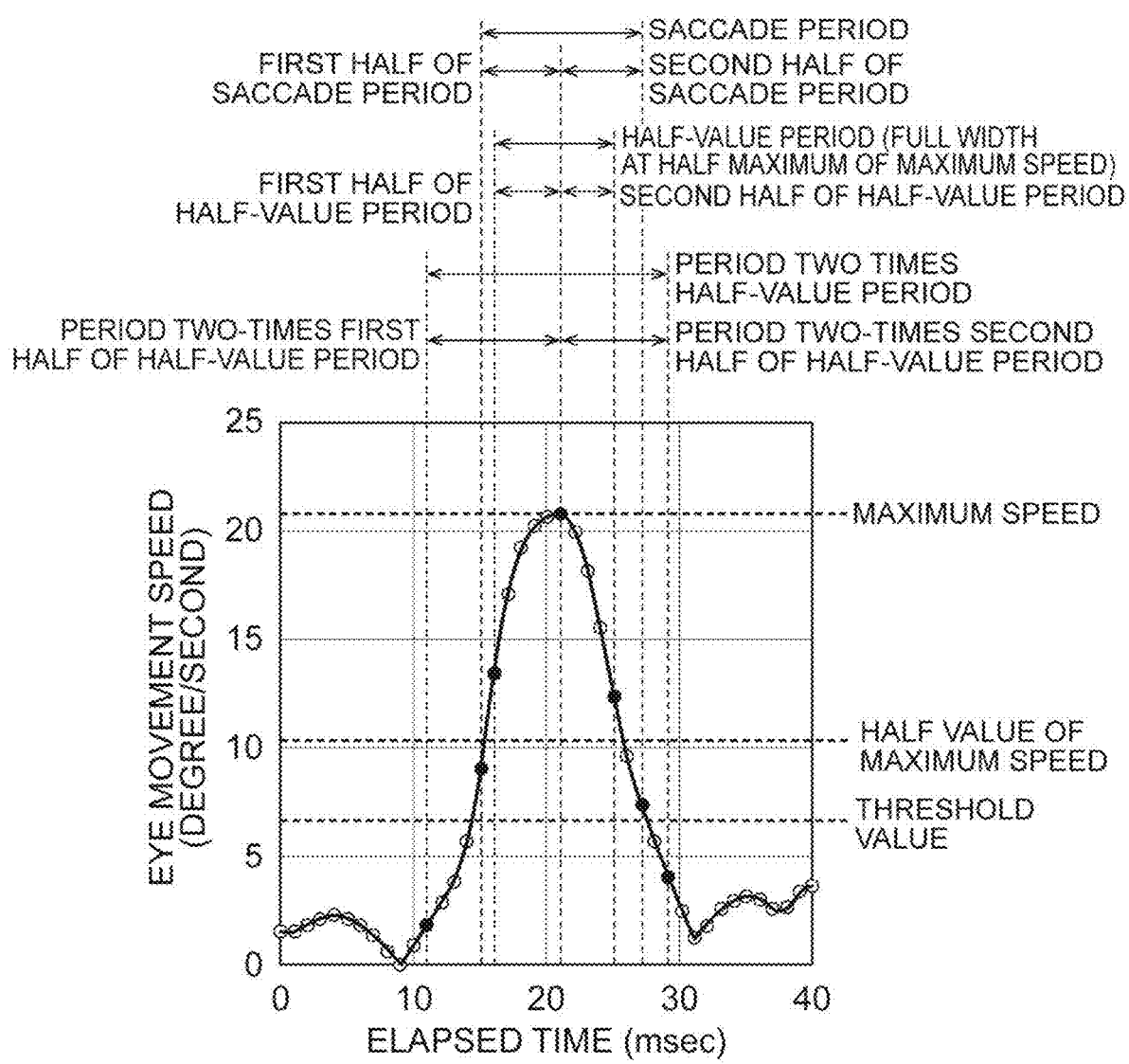
FIG. 2 is a graph illustrating eye movement speeds in a time series.

The feature amount calculating unit 23 receives an input of information indicating the eye movement speeds in a time series and the saccade period from the saccade period extracting unit 22. The feature amount calculating unit 23 sets a period including at least a part of the saccade period, which will be divided. The period which will be divided is, for example, the saccade period. Alternatively, the period which will be divided may be a half-value period (a period of the full width at half maximum) which is a period with a half-value width of the maximum speed of the eye movement speed. As illustrated in FIG. 2, the feature amount calculating unit 23 divides the period which will be divided into a first half period and a second half period at the time at which the eye movement speed reaches the maximum speed. The feature amount calculating unit 23 may set a first half period obtained by extending the first half period of the half-value period to the first half side (in a direction in which the time goes back) to double and a second half period obtained by extending the second half period of the half-value period to the second half side (in a direction in which time elapses) to double as the separate periods. In this case, the sum period of the first half period and the second half period, that is, two times the half-value period, is a period which will be divided.

The saccade period acquired using the threshold value indicates a general period which has also been used for previous researches, but is affected by the magnitude of the threshold value. Since the threshold value is set in consideration of noise, a period which is greater than the threshold value tends to be a partial period of saccadic movement and is not suitable for evaluating the saccade period. Therefore, as described above, the half-value period and a period of two times the half-value period may be used as a period for quantizing the whole saccadic movement instead of the saccade period. The former half-value period indicates a period in which an eye moves at a high speed. The variation tendency in speed can be guessed from three feature points of the maximum point and half values before and after the maximum speed. When the maximum speed is high and the half-value period is short, it refers to movement in a pulse signal form which is instantaneously completed. When the maximum speed is low and the half-value period is short, it refers to an instantaneous signal. The period with two times the latter half-value period indicates the period of the whole saccadic movement. This is a period including a period in which the eye moves at a lower speed than in the saccade period and the half-value period.

A start time and an end time of each period may be referred to as sampling points (times at which an image is captured) as illustrated in FIG. 2. A start time and an end time with the time resolution (the frame rate) of the camera 10 or higher can be calculated using a threshold value, a half value of a maximum speed, a half-value period, a ratio of values before and after each value, and the like and may be employed. Division of a period is not necessarily performed as described above and, for example, a period may be divided into two equal periods including a first half period and a second half period.

The feature amount calculating unit 23 calculates feature amounts in the first half period and the second half period. Examples of the feature amounts which are calculated include a saccade distance, a length of a period, an average speed of eye movement speeds, the standard deviation of eye movement speeds, and the standard deviation of accelerations. The presence or absence of an undulation of eye movement speeds, the number of undulations, and a maximum speed may be calculated as the feature amounts which are calculated. The undulation of eye movement speeds refers to a point at which the eye movement speed with an increasing tendency has changed to a decreasing tendency and a point at which the eye movement speed with a decreasing tendency has changed to an increasing tendency. These can be detected by searching for inversion in sign of the eye movement acceleration. Alternatively, the undulation of the eye movement speed may be extracted after determining whether to extract the undulation with reference to the time at which the sign of the eye movement acceleration has been inverted and the eye movement speeds before and after. When undulation of the eye movement speed which is extracted with changed extraction conditions and a plurality of undulations are observed, a speed ratio and a speed difference of the maximum speed thereof, a time interval from the maximum speed time to the maximum undulation speed, and the like may be calculated as feature amounts. The feature amounts other than the length of a period are calculated based on the eye movement speeds in a time series in each period.

The feature amounts may be calculated using moving state values other than the eye movement speeds. For example, when eye positions in a time series is used, a saccade direction, the standard deviation of the saccade directions, the sum of changes of the saccade directions, and the saccade direction at the maximum speed time may be calculated as feature amounts. In this case, information indicating eye positions in a time series along with the eye movement speeds is transmitted from the camera 10 to the computer 20.

The feature amount calculating unit 23 may calculate a new feature amount by comparison of the feature amounts, that is, the feature amount calculating unit 23 may calculate a ratio, a difference, or the like of a plurality of feature amounts and use the calculated ratio or difference as new feature amounts. For example, the feature amount calculating unit 23 may calculate a value of a ratio of a feature amount in the first half period and a feature amount in the second half period as for the same type of feature amounts as a new feature amount. Alternatively, the feature amount calculating unit 23 may calculate a value of a ratio of different types of feature amounts (for example, a ratio of the length of a period and the maximum speed of an eye movement speed) in the same period as a new feature amount.

All of the separate periods and the feature amounts after the division do not need to be used and a part thereof may be used. Feature amounts in the period which will be divided (a saccade period, a half-value period, and a period with two times the half-value period) may be calculated. The feature amount calculating unit 23 outputs the calculated feature amounts to the determination unit 24.

The determination unit 24 is determination means that determines a brain state of an examinee based on the feature amounts calculated by the feature amount calculating unit 23. Determination by the determination unit 24 using the feature amounts calculated by the feature amount calculating unit 23 is based on following knowledge which has been found by the inventor of the present invention. The knowledge has found by measurement of saccadic movement at a higher speed and with higher accuracy than in the previous researches.

Figure 3A:
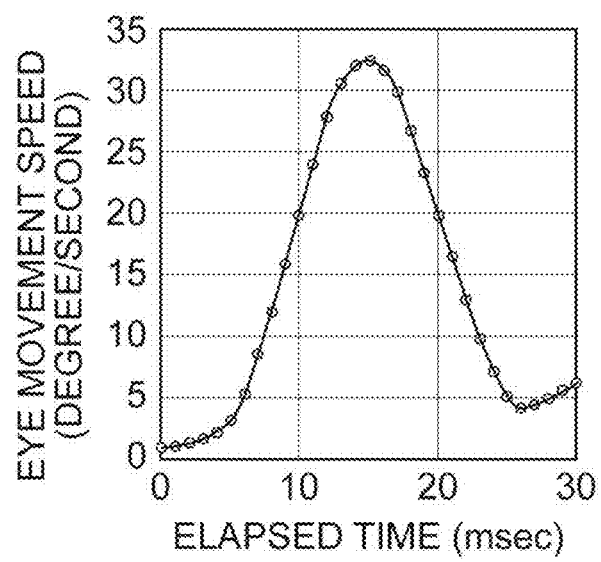
FIG. 3A is a graph illustrating eye movement speeds in a time series when movement of an eye is regular.
Figure 3B:
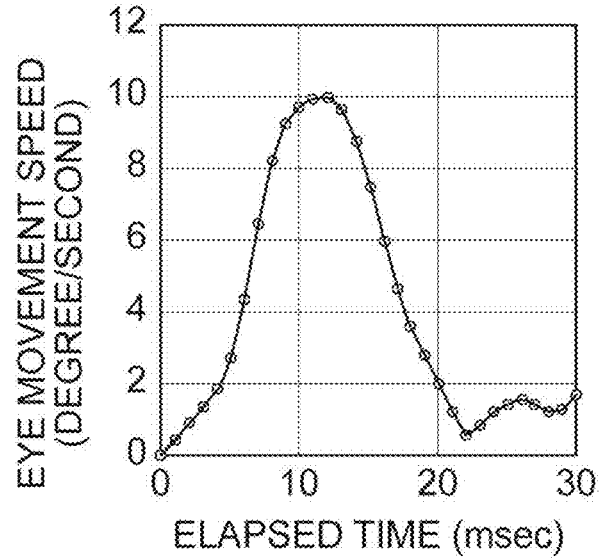
FIGS. 3B and 3C are graphs illustrating eye movement speeds in a time series when movement of an eye is irregular.
Figure 3C:
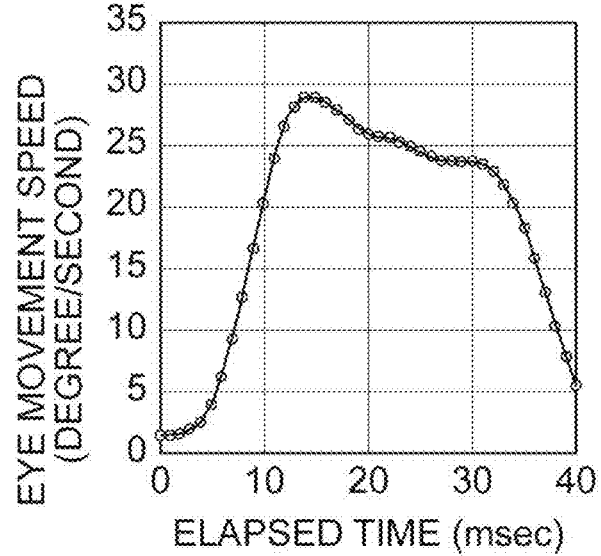

A micro-saccade is a motion which starts instantaneously and in which an eye movement speed increases monotonously, reaches a maximum speed, then decreases monotonously, and converges. In general, in a micro-saccade, an eye movement speed exhibits symmetric movement before and after the maximum speed time as illustrated in FIG. 3A. However, micro-saccades having less symmetry and moving irregularly are also observed as illustrated in FIGS. 3B and 3C. Examples of an irregular micro-saccade include a pattern in which movement does not converge rapidly after the movement speed reaches a maximum speed but converges after the eye position has changed continuously for a predetermined time, a pattern in which an eye movement speed does not increase monotonously but increases and decreases repeatedly until the eye movement speed reaches a maximum speed, and a pattern in which an eye movement speed does not decrease monotonously after the eye movement speed reaches a maximum speed but decreases while repeatedly increasing and decreasing. Such a micro-saccade having less symmetry and exhibiting irregular moment is more observed in eye movement measurement data of patients with a brain disease such as brain dysfunction than healthy persons. The embodiment of the invention considers such irregular eye movement. Feature amounts using the above-mentioned separate periods are obtained by quantizing the irregular eye movement. That is, feature amounts using the above-mentioned separate periods reflects the irregular eye movement more strongly than that when the non-separate period is used.

Figure 4A:
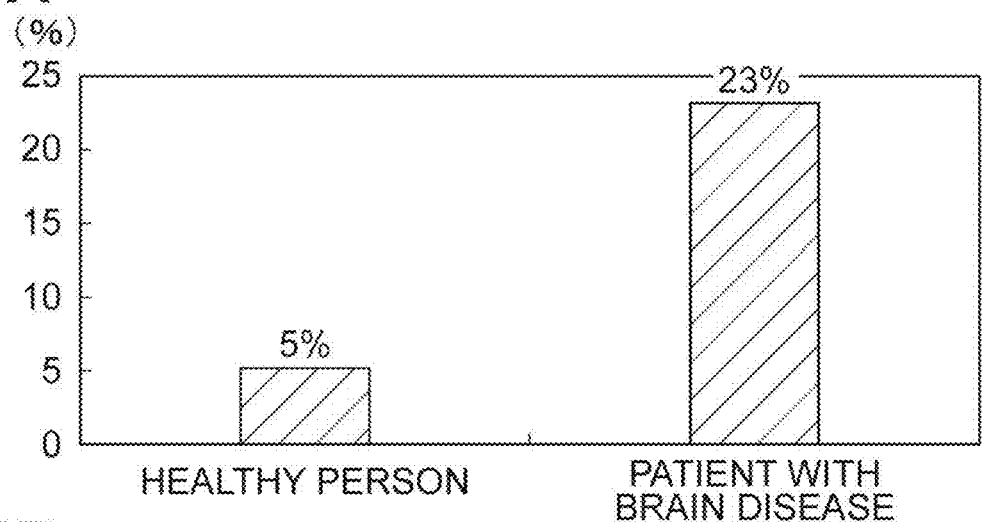
FIGS. 4A, 4B, and 4C are graphs illustrating frequencies in which feature amounts satisfy predetermined conditions for healthy persons and patients with a brain disease.
Figure 4B:
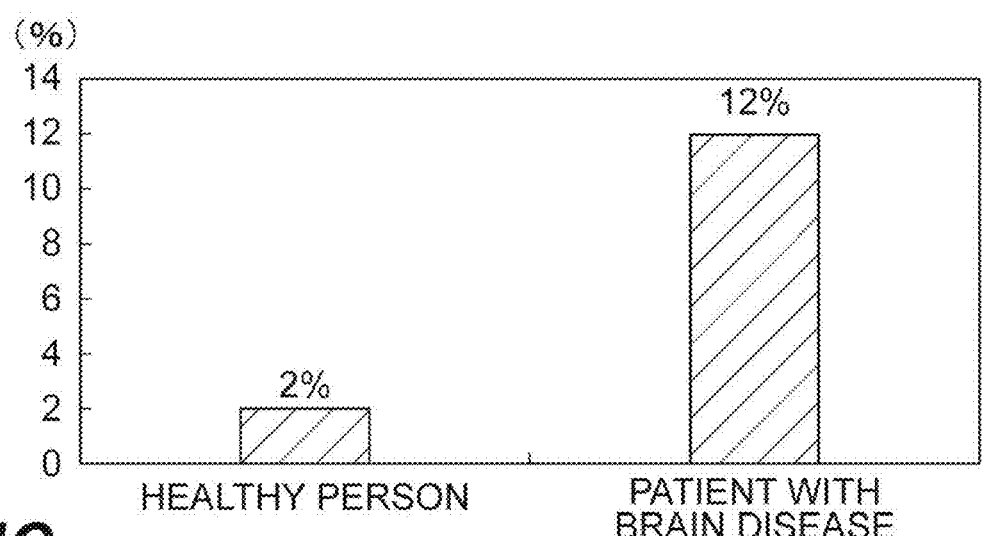
Figure 4C:
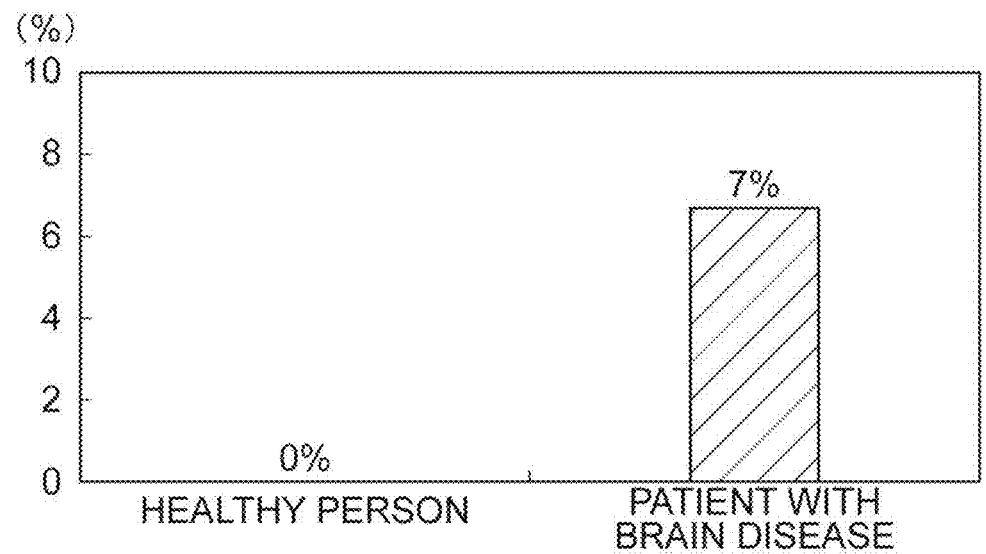

FIGS. 4A, 4B, and 4C illustrate examples in which differences between 22 healthy persons and 27 patients with a brain disease are evaluated using the feature amounts in this embodiment. A sorting threshold value is provided for each feature amount and frequencies (a proportion) of persons who are extracted using the sorting threshold value are collected. A value in which the magnitude relationship between cumulative frequency distributions of the healthy persons and the patients with a brain disease is inverted is employed as the sorting threshold value. FIG. 4A illustrates frequencies of persons in which a ratio of the length of a first half period and the length of a second half period of a half-value period (the length of the second half period/the length of the first half period) is equal to or greater than 1.3. The ratio represents that the lengths of the first half period and the second half period become equal to each other as the value becomes closer to 1 and the second half period is longer than the first half period as the value becomes greater than 1. This feature amount represents whether a micro-saccade exhibits movement is symmetric or asymmetric in the first half period and the second half period with respect to the maximum speed. As a result, micro-saccades of the patients with a brain disease exhibit tendency in which the second half of the half-value period is longer than the first half thereof when compared to that of the healthy persons. In consideration of the results of collection of undulations of the eye movement speeds along with the result, it is possible to ascertain whether there is irregular movement in the micro-saccades.

FIG. 4B illustrates frequencies in which there is undulation of an eye movement speed less than a half value of a maximum speed in a second half period of a period with two times a half-value period. It can be seen that the patients with a brain disease perform a micro-saccade in which an eye movement speed varies irregularly more than the healthy persons. FIG. 4C illustrates frequencies in which there is undulation of an eye movement speed after the maximum speed time in the saccade period extracted using the threshold value, that is, in the second half period. This irregular micro-saccade which is not observed for the healthy persons is much observed for 7% of the patients with a brain disease.

As described above, with the feature amounts calculated by the feature amount calculating unit 23, it is possible to determine whether some disorder occurs in the brain function of an examinee. The determination unit 24 performs such determination, for example, as follows. The determination unit 24 receives an input of feature amounts from the feature amount calculating unit 23. The determination unit 24 calculates a score for performing determination based on the feature amounts. For example, it is assumed that the score exhibits a higher likelihood that some disorder occurs in the brain function as the value of the score becomes higher. The determination unit 24 compares the individual feature amounts with the threshold value and increases the score (for example, +1) when the comparison result indicates that there is a higher likelihood that some disorder occurs in the brain function. When the comparison result does not indicate that there is a high likelihood that some disorder occurs in the brain function, the determination unit 24 decreases the score (for example, −1). The threshold value may be set and stored in the determination unit 24 depending on the types of the feature amounts in advance. For example, the threshold value is set to a value in which the magnitude relationship between the cumulative frequency distributions of the healthy persons and the patients with a brain disease is inverted in the feature amounts obtained from the eye measurement results of the healthy persons and the patients with a brain disease.

When a plurality of types of feature amounts are calculated, the determination unit 24 may calculate a feature amount for each of such feature amounts and take the sum thereof or use the individual features as the feature amounts. When a plurality of micro-saccades are extracted from one time of eye measurement, a feature amount is calculated for each micro-saccade and an average value thereof is used as a total score of the corresponding examinee. That is, the total score is calculated by the following equation.

$$\text{Total score} = \frac{\sum^{\text{Total number of}}_{\text{micro-saccades}} \sum^{\text{Total}}_{\text{feature values}} \text{Score for each feature value}}{\text{Total number of micro-saccades}}$$

When a plurality of micro-saccades are extracted, a cumulative value (a value which is not divided by the total number of micro-saccades in the equation) instead of the average value may be used as the total score.

The determination unit 24 compares the calculated total score with a threshold value and performs the determination based on the comparison result. The threshold value is set and stored in the determination unit 24 in advance. When the total score is equal to or greater than the threshold value, the determination unit 24 determines that some disorder occurs in the brain function of the examinee. When the total score is less than the threshold value, the determination unit 24 determines that some disorder does not occur in the brain function of the examinee.

The total score may be calculated using a method other than described above. For example, the total score may be calculated using a method using majority decision based on feature amounts or multivariable analysis such as main component analysis.

The determination unit 24 outputs the determination result. For example, the determination unit 24 causes a display device of the computer 20 to display information indicating the determination result. For example, this display is referred to by a user of the eye movement feature amount calculating system 1. The output from the determination unit 24 may be performed in an aspect other than described above. For example, the determination result may be transmitted and output to an external server or an external PC via a network such as Ethernet (registered trademark) using the TCP/IP (Transmission Control Protocol/Internet Protocol). At this time, the captured images and the calculated feature amounts may also be transmitted.

Determination by the determination unit 24 may be performed using a method other than described above. For example, feature amounts acquired from measurement results of eyes of healthy persons and patients with a brain disease are stored in a database in advance. Then, a distance which is used for cluster analysis such as a Mahalanobis distance between each of the feature amounts of a group of healthy persons and the feature amounts of a group of patients with a brain disease which are stored in the database and feature amounts of an examinee calculated by the feature amount calculating unit 23 may be calculated and the determination may be performed based on the calculated distances. The database may be stored outside the computer 20. In this case, the determination unit 24 refers to the database via a network such as the Internet. The configuration of the eye movement feature amount calculating system 1 has been described above.

Figure 5:
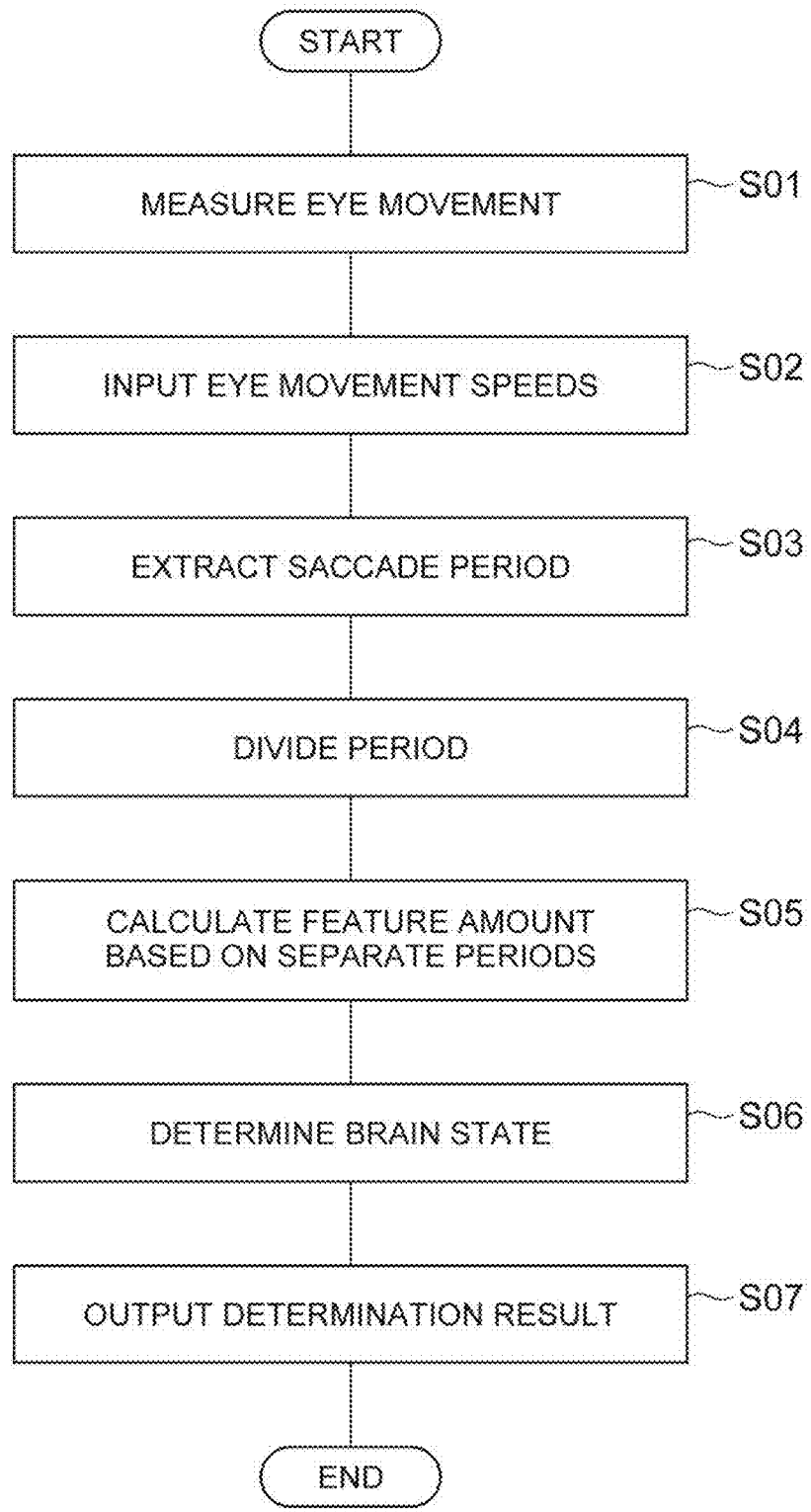
FIG. 5 is a flowchart illustrating processes (an eye movement feature amount calculating method) which are performed by the eye movement feature amount calculating system according to the embodiment of the invention.

Processes which are performed by the eye movement feature amount calculating system 1 (an operating method which is performed by the eye movement feature amount calculating system 1) according to this embodiment will be described below with reference to the flowchart illustrated in FIG. 5. First, measurement of eye movement of an examinee is performed by the camera 10 (S01, a moving state measuring step). Specifically, the camera 10 captures images of an eye of an examinee and calculates eye movement speeds in a time series from the captured images. Information indicating the calculated eye movement speeds in a time series is transmitted from the camera 10 to the computer 20. In the computer 20, the moving state input unit 21 receives and inputs the information indicating the eye movement speeds in a time series (S02, a moving state input step).

Subsequently, the saccade period extracting unit 22 extracts a saccade period in which the eye performs a micro-saccade based on time-series variation of the eye movement speeds (S03, a saccade period extracting step). Subsequently, the feature amount calculating unit 23 divides a period including at least a part of the saccade period into a plurality of periods (S04, a feature amount calculating step). Subsequently, the feature amount calculating unit 23 calculates feature amounts of eye movement of the examinee based on the separate periods (S05, a feature amount calculating step). Subsequently, the determination unit 24 determines a brain state of the examinee based on the calculated feature amounts (S07). Subsequently, the determination unit 24 outputs determination results (S07). The processes which are performed by the eye movement feature amount calculating system 1 according to this embodiment have been described above.

By using feature amounts based on the separate periods as described above, for example, it is possible to perform determination of a brain state or the like more appropriately than in a case in which feature amounts based on the whole saccade period are used. Accordingly, according to this embodiment, it is possible to more appropriately calculate feature amounts of eye movement which can be used for determination of a brain state or the like.

Figure 6:
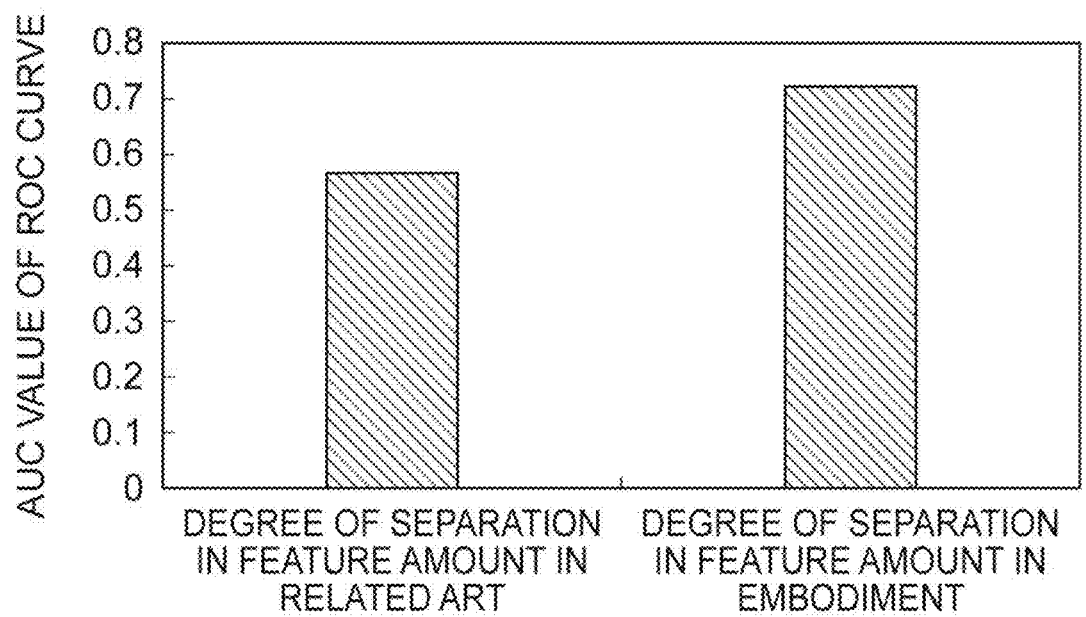
FIG. 6 is a graph illustrating degrees of separation when healthy persons and patients with a brain disease are separated in the embodiment and the related art.

FIG. 6 illustrates a degree of separation when healthy persons and patients with a brain disease are separated using feature amounts in this embodiment and a degree of separation when healthy persons and patients with a brain disease are separated using feature amounts in the related art (feature amounts based on a non-divided period) without using the feature amounts in this embodiment. An area under the curve (AUC) value of a receiver operating characteristic (ROC) curve is used for quantitative evaluation of the degree of separation. The AUC value has a value in a range from 0.5 to 1.0 and the degree of separation between two groups becomes higher as the value becomes higher. The degree of separation between the two groups is low when the AUC value ranges from 0.5 to 0.7, is middle when the AUC value ranges from 0.7 to 0.9, and is high when the AUC value ranges from 0.9 to 1.0. As the result of evaluation, the AUC value in the total score using the feature amounts in the related art is 0.58, but the AUC value increases to 0.73 by adding the feature amounts in this embodiment. A practical degree of separation is obtained using the feature amounts in this embodiment.

Division of a period in this embodiment may be performed based on time-series variation of eye movement speeds. Specifically, a period may be divided into periods before and after a maximum speed of the eye movement speed. According to this configuration, it is possible to appropriately and certainly perform division of a period and to more appropriately calculate feature amounts of eye movement which can be used for determination of a brain state or the like. Here, it is not necessary to perform division of a period as described above and, for example, a period which will be divided equally.

As in this embodiment, a value as a comparison result of the values in the separate periods, for example, a ratio or difference value, may be used as a feature amount. According to this configuration, it is possible to more appropriately calculate feature amounts of eye movement which can be used for determination of a brain state or the like.

As in this embodiment, an eye movement speed may be used as the moving state value. According to this configuration, it is possible to appropriately and certainly calculate feature amounts of eye movement. Here, values other than the eye movement speeds may be used as moving state values as long as they are values in a time series indicating each a moving state of an eye. For example, a moving distance, a moving direction, or an acceleration may be used as the moving state value. A plurality of types of moving state values may be combined and used.

A brain state of an examinee may be determined using feature amounts calculated as in this embodiment. According to this configuration, it is possible to appropriately determine a brain state of an examinee using the calculated feature amounts. The determination does not need to be performed and only feature amounts may be calculated in the eye movement feature amount calculating system 1. In this case, determination of a brain state may be performed by a system or device other than the eye movement feature amount calculating system 1. Alternatively, the determination may be performed by an expert such as a doctor. The feature amounts calculated by the eye movement feature amount calculating system 1 may be used for applications other than determination of a brain state. For example, the feature amounts calculated by the eye movement feature amount calculating system 1 may be used for quantitative evaluation of saccadic movement of an eye.

As in this embodiment, for example, the camera 10 may measure a moving state of an eye and calculate an eye movement speed. According to this configuration, it is possible to certainly input an eye movement speed and to satisfactorily realize an embodiment of the invention. In the invention, the eye movement feature amount calculating system 1 may be constituted by only the computer 20 according to this embodiment as long as an eye movement speed can be input. That is, calculation of an eye movement speed may be performed by a system or device other than the eye movement feature amount calculating system 1.

In this embodiment, eye movement which is measured by the eye movement feature amount calculating system 1 is a micro-saccade, but saccadic movement other than a micro-saccade may be used as a measurement object, that is, an object of which feature amounts will be calculated. For example, eye movement which is referred to as square wave jerks may be used as a measurement object.

Figure 7:
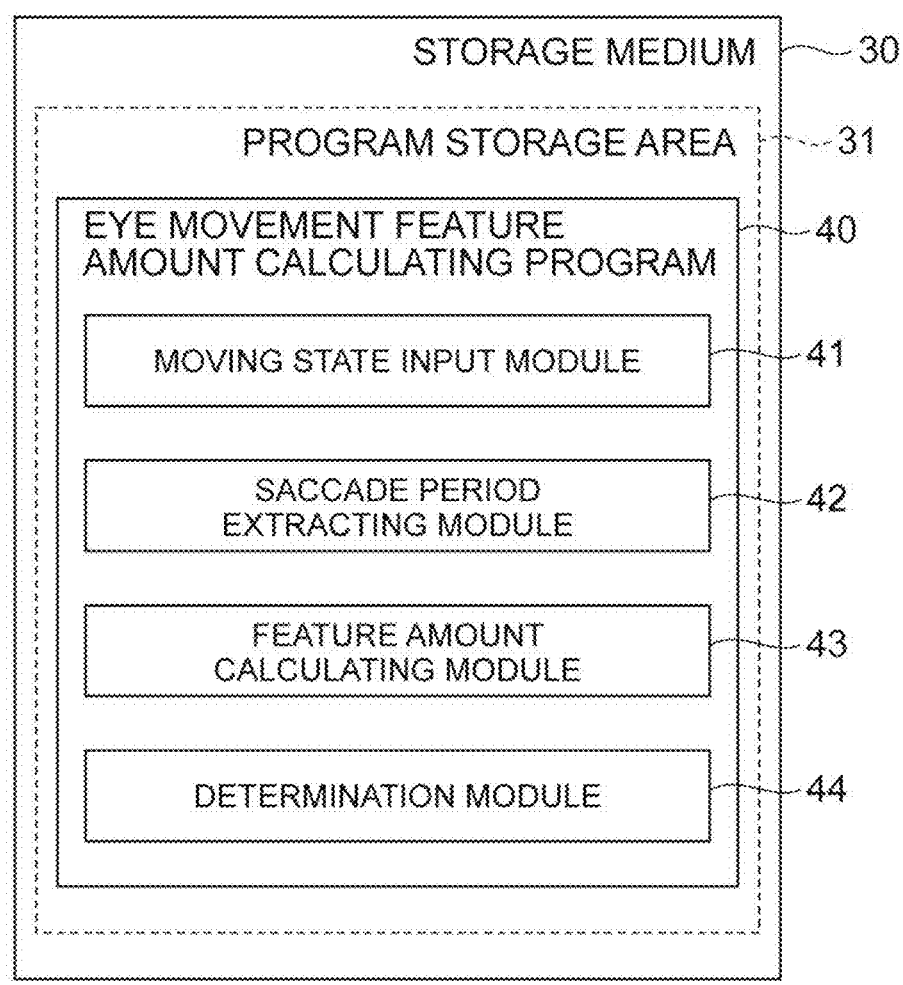
FIG. 7 is a diagram illustrating a configuration of an eye movement feature amount calculating program according to the embodiment of the invention along with a storage medium.

An eye movement feature amount calculating program for causing the computer 20 to perform the above-mentioned processes will be described below. As illustrated in FIG. 7, an eye movement feature amount calculating program 40 is stored in a program storage area 31 formed in a storage medium 30 which is inserted into and accessed by a computer or which is included in the computer.

The eye movement feature amount calculating program 40 includes a moving state input module 41, a saccade period extracting module 42, a feature amount calculating module 43, and a determination module 44. Functions which are realized by executing the moving state input module 41, the saccade period extracting module 42, the feature amount calculating module 43, and the determination module 44 are the same as the functions of the moving state input unit 21, the saccade period extracting unit 22, the feature amount calculating unit 23, and the determination unit 24 of the computer 20.

A part or all of the eye movement feature amount calculating program 40 may be transmitted via a transmission medium such as a communication line and may be received and recorded (including installation) by another device. Each module of the eye movement feature amount calculating program 40 may be installed in one of a plurality of computers instead of one computer. In this case, the above-mentioned processes of the eye movement feature amount calculating program 40 is performed by a computer system including the plurality of computers.

What is claimed is:

1. An eye movement feature amount calculating system comprising circuitry configured to:
   input moving state values in a time series each indicating a moving state of an eye of a subject;
   extract a saccade period in which the eye performs saccadic movement based on time-series variation of the moving state values; and
   divide a period including at least a part of the saccade period into a plurality of periods based on the extracted saccade period and calculate a feature amount of eye movement of the subject based on the separate periods.

2. The eye movement feature amount calculating system according to claim 1, wherein the circuitry is further configured to divide the period including at least a part of the saccade period into a plurality of periods based on the time-series variation of the moving state values in the saccade period.

3. The eye movement feature amount calculating system according to claim 2, wherein the circuitry is further configured to divide the period into a first half period and a second half period at a time at which the moving state value in the saccade period is the maximum.

4. The eye movement feature amount calculating system according to claim 1, wherein the circuitry is further configured to calculate a value based on the moving state values for each of the separate periods and calculate the feature amount of the eye movement of the subject by comparing the calculated values for the separate periods.

5. The eye movement feature amount calculating system according to claim 1, wherein the circuitry is further configured to input a value indicating a speed of the eye as the moving state value.

6. The eye movement feature amount calculating system according to claim 1, further comprising determination means that determines a brain state of the subject based on the feature amount.

7. The eye movement feature amount calculating system according to claim 1, wherein the circuitry is further configured to measure moving states of the eye of the subject and generate the moving state values.

8. An eye movement feature amount calculating method comprising:
   inputting moving state values in a time series indicating a moving state of an eye of a subject;
   extracting a saccade period in which the eye performs saccadic movement based on time-series variation of the moving state values; and
   dividing a period including at least a part of the saccade period into a plurality of periods based on the extracted saccade period and calculating a feature amount of eye movement of the subject based on the separate periods.

9. A non-transitory computer-readable storage medium storing an eye movement feature amount calculating program causing a computer to execute:
   a moving state input function of inputting moving state values in a time series indicating a moving state of an eye of a subject;
   a saccade period extracting function of extracting a saccade period in which the eye performs saccadic movement based on time-series variation of the moving state values; and
   a feature amount calculating function of dividing a period including at least a part of the saccade period into a plurality of periods based on the extracted saccade period and calculating a feature amount of eye movement of the subject based on the separate periods.

* * * * *